(12) United States Patent
Scampoli et al.

(10) Patent No.: US 9,974,916 B2
(45) Date of Patent: May 22, 2018

(54) SIDESTREAM RESPIRATORY GAS SAMPLING SYSTEM WITH FLEXIBLE ACCESSORIES AND REMOVABLE WATER TRAP

(71) Applicant: KONINKLIJKE PHILIPS N.V., Eindhoven (NL)

(72) Inventors: David Scampoli, South Glastonbury, CT (US); Brian Matthew Fudge, Middlefield, CT (US); Bartosz Korec, Palm Harbor, FL (US); Richard Cipriano, Dunedin, FL (US); Philip D'Almada Remedios, Palm Harbor, FL (US)

(73) Assignee: Koninklijke Philips N.V., Eindhoven (NL)

( * ) Notice: Subject to any disclaimer, the term of this patent is extended or adjusted under 35 U.S.C. 154(b) by 410 days.

(21) Appl. No.: 14/420,991

(22) PCT Filed: Aug. 9, 2013

(86) PCT No.: PCT/IB2013/056529
§ 371 (c)(1),
(2) Date: Feb. 11, 2015

(87) PCT Pub. No.: WO2014/027290
PCT Pub. Date: Feb. 20, 2014

(65) Prior Publication Data
US 2015/0217077 A1 Aug. 6, 2015

Related U.S. Application Data

(60) Provisional application No. 61/683,402, filed on Aug. 15, 2012.

(51) Int. Cl.
*A61B 5/08* (2006.01)
*B65D 81/00* (2006.01)
(Continued)

(52) U.S. Cl.
CPC ......... *A61M 16/0808* (2013.01); *A61B 5/082* (2013.01); *A61B 5/097* (2013.01);
(Continued)

(58) Field of Classification Search
USPC .............................. 600/532, 543; 128/202.27
See application file for complete search history.

(56) References Cited

U.S. PATENT DOCUMENTS

| 4,446,869 A | 5/1984 | Knodle |
| 5,131,387 A | 7/1992 | French et al. |

(Continued)

FOREIGN PATENT DOCUMENTS

EP 0707827 A1 4/1996

*Primary Examiner* — Christian Jang
*Assistant Examiner* — Mitchell E Alter (57) ABSTRACT

A removable water trap device (110) removes moisture from a respiratory gas stream from a patient interface assembly (140), enabling monitoring of gas within the respiratory gas stream by an analysis bench (120). The device includes a housing (111), an upstream water trap connector (115), and a filter assembly (360). The housing includes a first portion (210) insertably attachable to a tether assembly receptacle (132) to connect the device to the analysis bench for delivering the gas stream via a tether line (136). The upstream water trap connector is attachable to a downstream patient interface connector (141, 143) in a sample flow line (145, 148) of the patent interface assembly for receiving the gas stream via the sample flow line. The filter assembly is insertably contained within the housing and configured to remove moisture from the gas stream, the filter assembly including a downstream water trap connector (116) attachable with the tether line within the tether assembly receptacle. The filter assembly is replaceable independently of replacement of the patient interface assembly.

20 Claims, 8 Drawing Sheets

(51) Int. Cl.
    *A61M 16/08*    (2006.01)
    *A61B 5/097*    (2006.01)
    *A61M 16/00*    (2006.01)
    *A61M 16/06*    (2006.01)
    *G01N 33/00*    (2006.01)
    *A61M 16/10*    (2006.01)

(52) U.S. Cl.
    CPC .... *A61M 16/0057* (2013.01); *A61M 16/0666* (2013.01); *A61M 16/085* (2014.02); *A61M 16/0816* (2013.01); *G01N 33/0014* (2013.01); *A61M 2016/103* (2013.01); *A61M 2202/04* (2013.01); *A61M 2205/7536* (2013.01)

(56) References Cited

U.S. PATENT DOCUMENTS

| | | | |
|---|---|---|---|
| 6,117,214 A | 9/2000 | Peter et al. | |
| 6,390,987 B1 | 5/2002 | Graham | |
| 6,896,713 B1* | 5/2005 | Eckerbom | A61B 5/097 422/84 |
| 2004/0060443 A1* | 4/2004 | Richardson | A61B 5/097 96/108 |
| 2006/0086254 A1 | 4/2006 | Fudge et al. | |
| 2007/0062313 A1* | 3/2007 | Rich | A61B 5/097 73/863.23 |
| 2008/0173306 A1 | 7/2008 | Peter et al. | |
| 2011/0283884 A1* | 11/2011 | Larsen | A61M 16/106 95/25 |

* cited by examiner

SIDESTREAM RESPIRATORY GAS SAMPLING SYSTEM WITH FLEXIBLE ACCESSORIES AND REMOVABLE WATER TRAP

CROSS-REFERENCE TO PRIOR APPLICATIONS

This application is the U.S. National Phase application under 35 U.S.C. § 371 of International Application No. PCT/IB2013/056529, filed on Aug. 9, 2013, which claims the benefit of U.S. Provisional Patent Application No. 61/683,402, filed on Aug. 15, 2012. These applications are hereby incorporated by reference herein.

BACKGROUND

A ventilator delivers a flow of pressurized gas, such as air and/or a mixture of air and extra (supplemental) oxygen, to the airway of a patient in order to assist in or substitute for the patient's breathing. A ventilator operates cyclically, such that the gas is provided to the patient during an inspiratory phase (corresponding to inhalation) and received from the patient during a subsequent expiratory phase (corresponding to exhalation). A sidestream gas analyzer diverts a portion of the patient's respired gases, which are inhaled and exhaled by the patient (respiratory gas stream) during mechanical ventilation or normal respiration, to a sensor, such as a gas analysis bench, through sampling tubes, including a patient airway interface and an extension line, for example.

The sensor may be used to detect and analyze at least one gas in the respiratory gas stream, such as carbon dioxide ($CO_2$). However, the presence of moisture generally affects the accurate detection of the various gases in the respiratory gas stream. A water filter or water trap is used to remove or reduce the moisture from the respiratory gas stream. The water filter or trap is often included among patient accessories in a disposable patient interface of a conventional sidestream respirator gas analysis system, and is therefore discarded after each use, along with other patient accessories, such as the airway and a cannula, for example. In addition, a sampling chamber receives the dried respiratory gas stream from the water trap filter and presents the sample gas in a controlled volume to the sidestream gas analysis bench for analysis. Similar to the water trap, the sampling chamber may also be included in the patient interface of a conventional sidestream respirator gas analysis system, and thus is discarded after each use. Such sidestream sampling accessories burden the disposable patient interface with the cost of the water trap and sampling chamber.

SUMMARY

In one aspect of the invention, a removable water trap device removes moisture from a respiratory gas stream received from a patient interface assembly, enabling monitoring of at least one gas within the respiratory gas stream by an analysis bench. The device includes a housing, an upstream water trap connector, and a filter assembly. The housing includes a first portion insertably attachable to a tether assembly receptacle to enable connection of the device to the analysis bench for delivering the respiratory gas stream via a tether line. The upstream water trap connector is attachable to a downstream patient interface connector of a sample flow line in the patent interface assembly for receiving the respiratory gas stream via the sample flow line. The filter assembly is insertably contained within the housing and configured to remove moisture from the respiratory gas stream, the filter assembly including a downstream water trap connector attachable with the tether line within the tether assembly receptacle. The filter assembly is replaceable independently of replacement of the patient interface assembly.

In another aspect of the invention, a sidestream respiratory gas analysis system includes a removable water trap for removing moisture from a respiratory gas stream received from a patient interface assembly; a gas analysis bench for detecting and analyzing at least one gas in the respiratory gas stream; and a tether assembly connected between the gas analysis bench and the patient interface assembly for providing the respiratory gas stream to the gas analysis bench. The tether assembly includes a tether assembly receptacle configured to insertably receive the water trap. The water trap includes a housing having a first portion insertable into a receptacle opening in the tether assembly receptacle, enabling delivery of the respiratory gas stream to the gas analysis bench via the tether assembly; a filter assembly insertable into the housing and configured to remove moisture from the respiratory gas stream; a downstream water trap connector for connecting the water trap to the tether assembly via the tether assembly receptacle for delivering the respiratory gas, with the moisture removed; and an upstream water trap connector for connecting the water trap to the patient interface assembly for receiving the respiratory gas stream.

In yet another aspect of the invention, a removable water trap device for removing moisture from a respiratory gas stream received from a patient interface assembly, enabling monitoring of at least one gas within the respiratory gas stream by an analysis bench, includes a housing, a filter assembly, and a connector. The housing includes first and second portions, the first portion being insertable into an opening in a tether assembly receptacle, enabling connection of the water trap device to the analysis bench for delivering the respiratory gas stream via a tether line. The housing defines grooves configured to slidably communicate with corresponding guide bumps protruding from an inner surface of the opening in the tether assembly receptacle. Each of the grooves is curved, requiring application of a turning motion of the housing to lock the first portion of the housing into the tether assembly receptacle. The filter assembly is insertably contained within the housing and configured to remove moisture from the respiratory gas stream. The filter assembly includes a seal tip configured to connect to the tether line within the tether assembly receptacle. The connector includes the second portion of the housing, and is attachable to a complementary connector of the patient interface assembly for receiving the respiratory gas stream via an extension line.

DETAILED DESCRIPTION

In the following detailed description, for purposes of explanation and not limitation, example embodiments disclosing specific details are set forth in order to provide a thorough understanding of an embodiment according to the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known devices and methods may be omitted so as to not obscure the description of the example embodiments. Such methods and devices are clearly within the scope of the present teachings.

Figure 1:
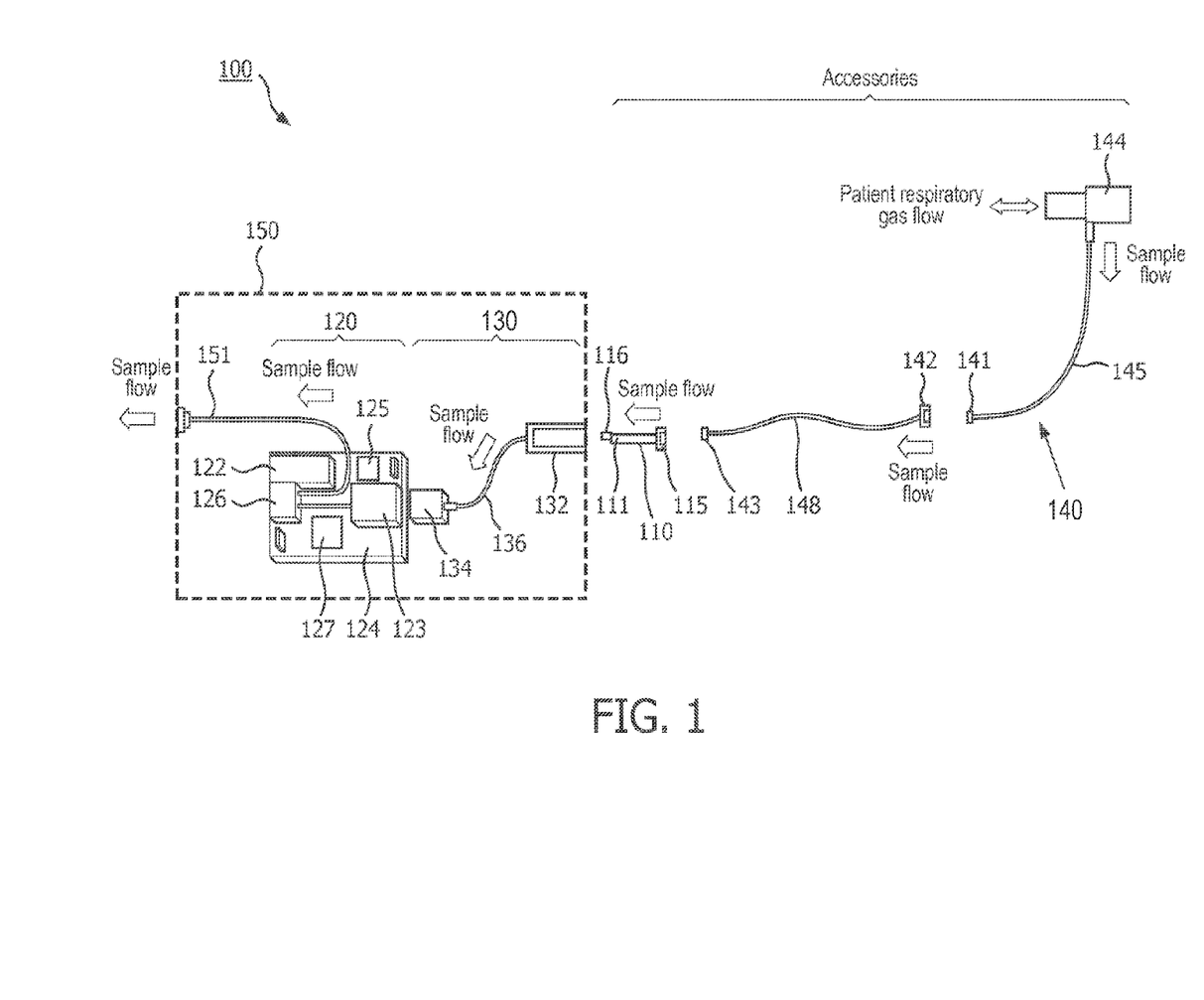
FIG. 1 is a functional block diagram of a sidestream respiratory gas analysis system, which includes a removable water trap, according to a representative embodiment.

FIG. 1 is a functional block diagram of a sidestream respiratory gas analysis system, which includes a removable water trap, according to a representative embodiment.

Referring to FIG. 1, sidestream respiratory gas analysis system 100 includes removable filter or water trap 110, module assembly or gas analysis bench 120, tether assembly 130, and patient interface assembly 140. The gas analysis bench 120 and the tether assembly 130 may be included in a host device 150. Generally, as shown by arrows indicating Sample Flow, a sampled respiratory gas stream is received from the patient via the patient interface assembly 140, passed to the gas analysis bench 120 via the water trap 110, analyzed at the detector 125, and exits the host device 150 through exhaust tube 151.

The water trap 110 removes moisture from a respiratory gas stream received from the patient interface assembly 140. The water trap 110 may be replaceable, published on Nov. 6, 2014, as U.S. Patent Application Pub. No. 2014/0326081, which is hereby incorporated by reference. The water trap 110 includes a housing 111, a portion of which is attachable (e.g., by insertion) to a tether assembly receptacle 132 in the tether assembly 130. The water trap 110 further includes an upstream water trap connector 115 and a downstream water trap connector 116 at opposite ends of the housing 111. The upstream water trap connector 115 connects to a sample flow line of the patient interface assembly 140 via a downstream patient interface connector. Examples of the sample flow line include an (optional) extension line 148 and an airway 145 of the patient interface assembly 140. The upstream water trap connector 115 is configured to connect to the extension line 148 via a downstream patient interface connector 143 (as depicted in FIG. 1), or directly to the airway 145 via a downstream patient interface connector 141. The downstream water trap connector 116 connects to a tether line 136 via the water trap receptacle 132 in the tether assembly 130. The water trap 110 may be embodied as a disposable filter cartridge, for example, attachable to the tether assembly receptacle 132 and used for one or more patients, regardless of whether elements of the patient interface assembly 140 are changed or replaced. Details of water trap 110 are described below with reference to FIGS. 2-9.

The tether assembly 130 is connected between the water trap 110 and the gas analysis bench 120 for providing the filtered respiratory gas stream to the gas analysis bench 120. The tether assembly 130 includes the tether assembly receptacle 132, which may define an opening configured to receive an insertable portion of the housing 111 of the water trap 110. The tether assembly 130 further includes a sampling chamber or sample cell 134 connected to the tether assembly receptacle 132 via the tether line 136. The sample cell 134 may be an optical sample cell, for example, that presents the sample gas in a controlled (known) volume to the sidestream gas analysis bench 120 for analysis. In the depicted embodiment, the sample cell 134 is removably connectable to the gas analysis bench 120. For example, the gas analysis bench 120 may include a sample cell receptacle 123 configured to insertably receive the sample cell 134, as shown in the depicted example. In the depicted embodiment, the sample cell 134 is a field replaceable item, and internal to the gas analysis bench 120. It is intended to be replaced only as necessary. In other configurations, the sample cell 134 may be externally removable for ease of replacement. Alternatively, the sample cell 134 may be included as part of the disposable patient interface assembly 140.

In the depicted embodiment, the gas analysis bench 120 includes a pump motor 122, a pump head 126, a sample cell receptacle 123, a detector 125, and a processor 127, all or some of which are mounted to a printed circuit board (PCB) 124 to enable detection and analysis of at least one gas, such as $CO_2$, in the respiratory gas stream. The pump motor 122 and the pump head 126 pump the respiratory gas stream through the sample cell 134, to the sample cell receptacle 123, and out the exhaust tube 151. The detector 125, which is part of the sample cell receptacle 123 or which may be incorporated onto the PCB of the gas analysis bench 120, receives a signal through the respiratory gas stream presented by the sample cell 134, and detects the amount of at least one gas, such as $CO_2$, in the respiratory gas stream. The detector 125 may include, for example, a photodiode detector, a photoconductive detector, or a photovoltaic or pyroelectric detector that is sensitive to the spectral range of the gas being measured. For example, for the detectors may be lead selenide, platinum silicide, or indium antimonide.

The processor 127 is configured to control operations of the various components of the gas analysis bench 120, including the detector 125, for analyzing the detection results. As will be appreciated by those skilled in the art, the processor 127 may be physically implemented, at least in part, using a software-controlled microprocessor, hard-wired logic circuits, or a combination thereof. For example, the processor 127 may be implemented as a microprocessor configured to execute one or more software algorithms, including gas flow, detection and analysis processes, in conjunction with a memory (not shown), to provide and/or control functionality of sidestream respiratory gas analysis system 100. That is, the processor 127 may include a nonvolatile memory for storing executable software code that allows it to perform the various functions of sidestream respiratory gas analysis system 100 and the respiratory gas detection and analysis process, discussed herein. The gas analysis bench 120 may further include a user interface (not shown) to enable control and programming of the processor 127, a display (not shown) for indicating the analysis results in real time or near real time and/or a memory (not shown) for storing the analysis results.

The patient interface assembly 140 is connected between the patient and the water trap 110. The patient interface assembly 140 includes patient accessories, such as cannula 144 and airway 145. The cannula 144 may be a nasal cannula, a nasal-oral sampling cannula, or a nasal-oral with oxygen delivery nasal cannula, for example. Notably, the patient accessories do not include a water trap, such as a conventional disposable, one-time use water trap, the functionality of which is otherwise provided by the removable water trap 110, discussed. Also, in various embodiments, the patient accessories may not include a conventional disposable, one-time use sample cell, the functionality of which is otherwise provided by the removable sample cell 134, discussed above. The patient interface assembly 140 further includes the extension line 148, which may include a dryer line formed of NAFION®, for example. The extension line 148 includes upstream patient interface connector 142 configured to connect with downstream patient interface connector 141, and the downstream patient interface connector 143 configured to connect with the upstream water trap connector 115 of the water trap 110. Each of the downstream patient interface connectors 141 and 143 and the upstream patient interface connector 142, as well as the upstream water trap connector 115 of the water trap 110, may be quick release connectors for simplifying assembly and disassembly of the sidestream respiratory gas analysis system 100, as discussed below. In an alternative embodiment, the patient interface assembly 140 may be a mainstream gas sampling adapter for use on intubated patients. Also, in various configurations, patient interface assembly 140 may not use the extension line 148, in which case the upstream water trap connector 115 may be connected directly to the downstream patient interface connector 141.

Figure 2:
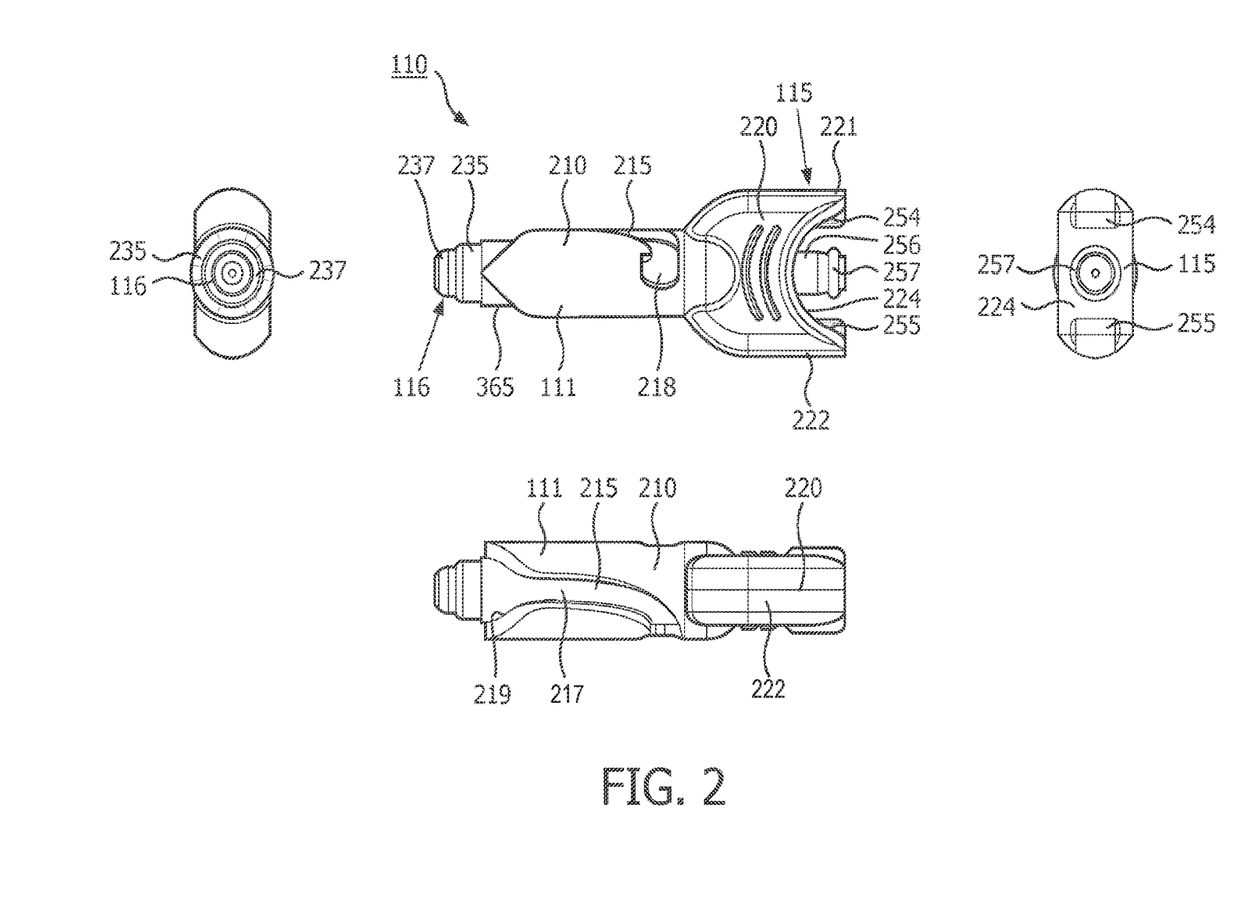
FIG. 2 provides perspective views of a removable water trap, according to a representative embodiment.
Figure 3:
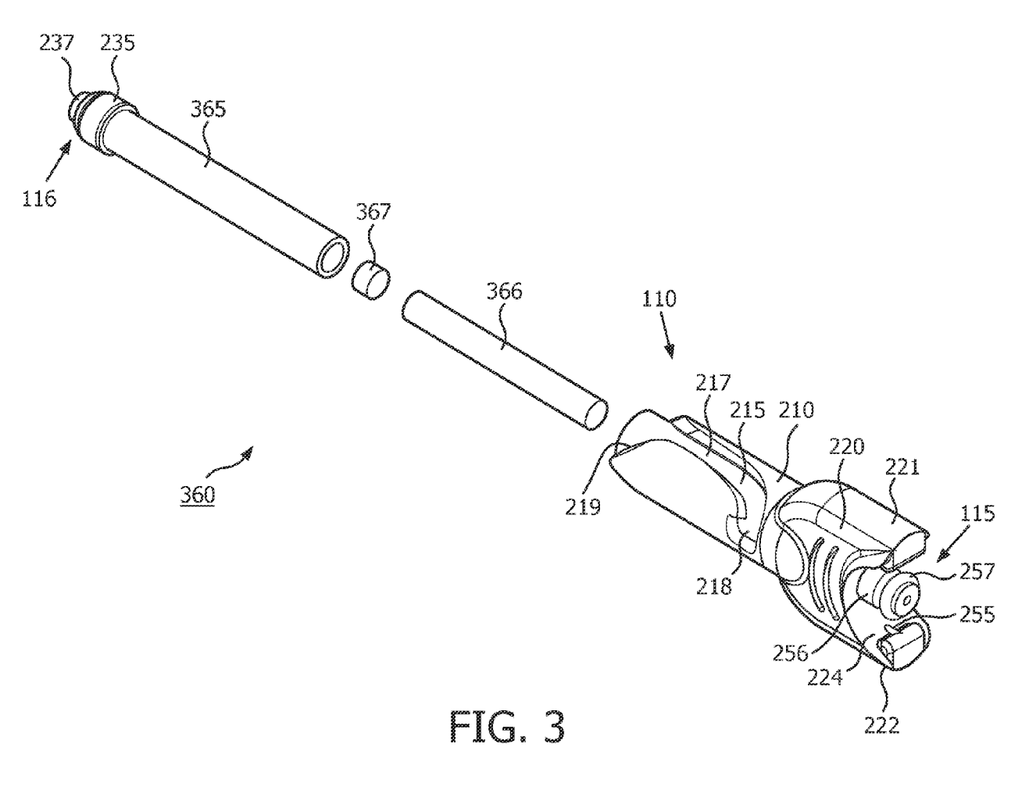
FIG. 3 is an exploded perspective view of a removable water trap, according to a representative embodiment.
Figure 4:
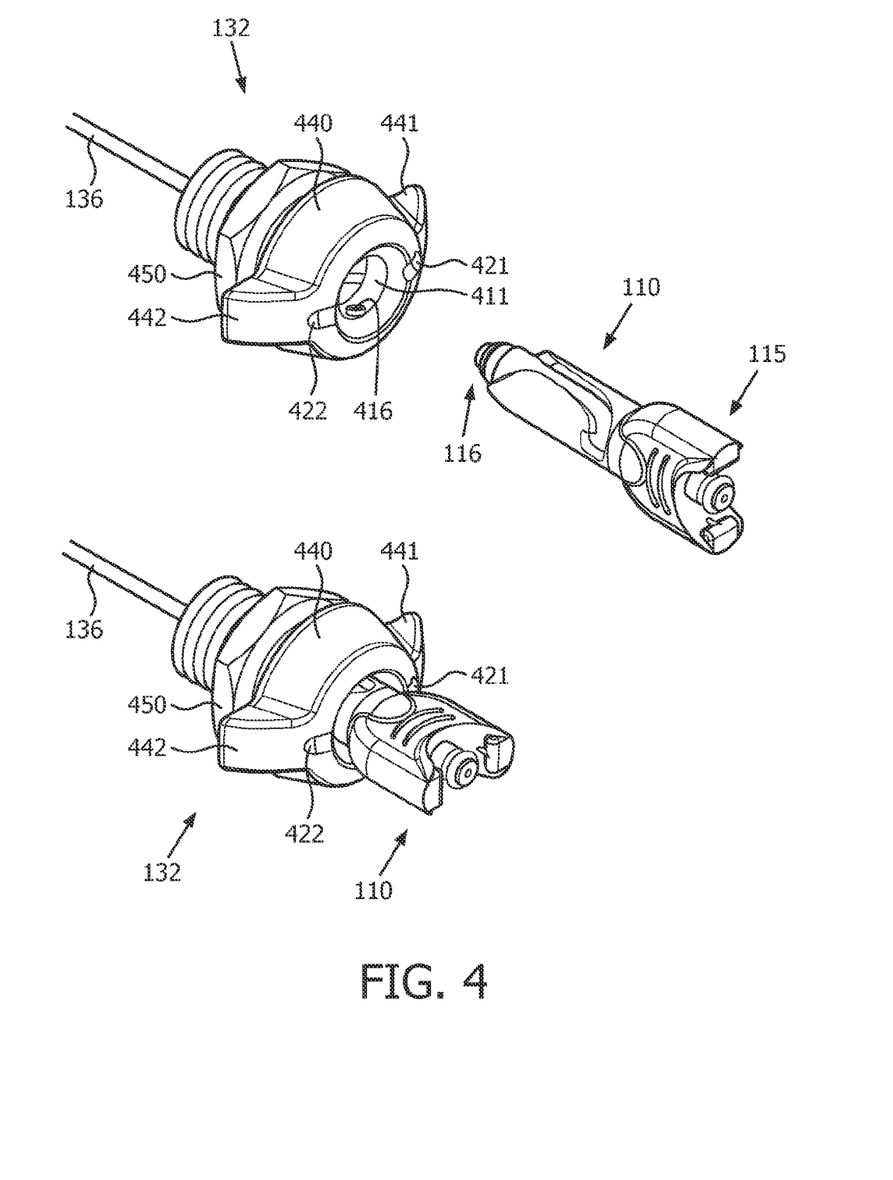
FIG. 4 provides perspective views of a removable water trap and a tether assembly receptacle, in disconnected and connected states, according to a representative embodiment.
Figure 5:
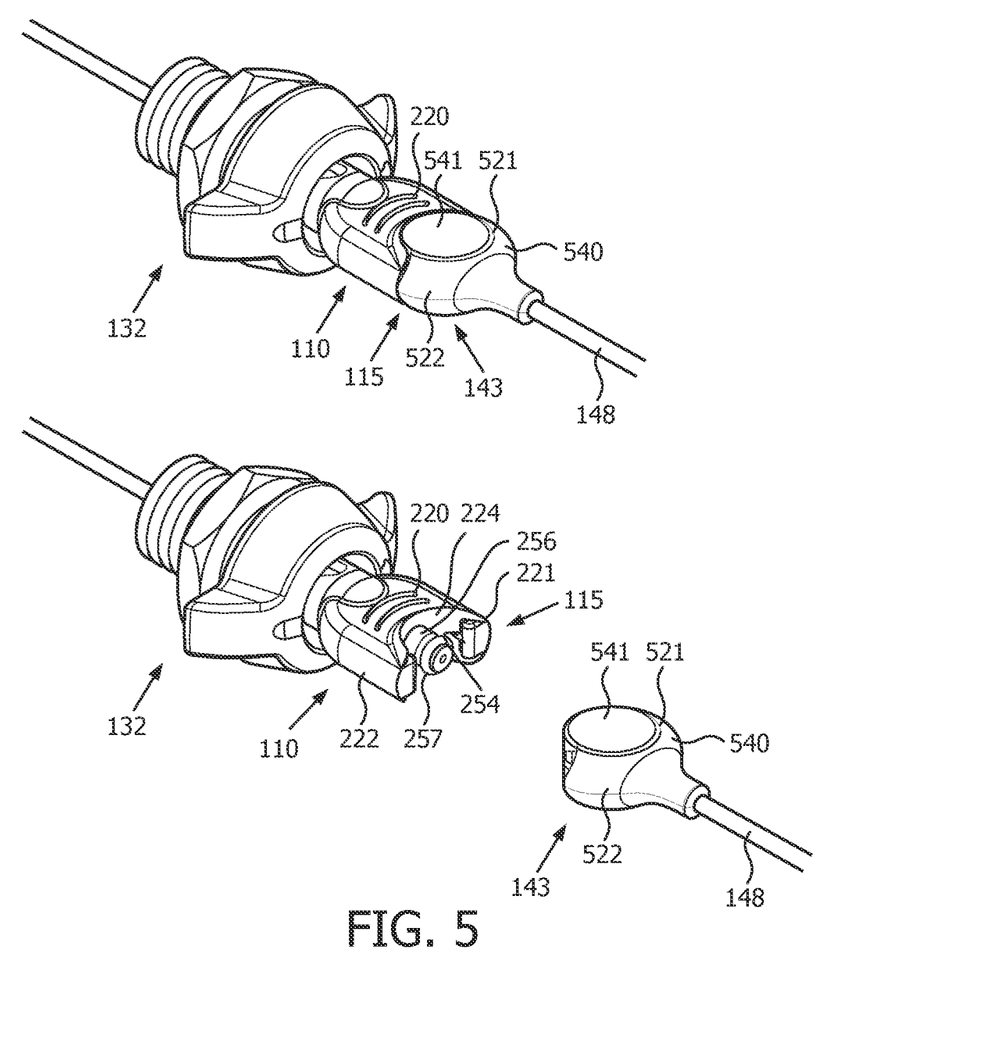
FIG. 5 provides perspective views of a removable water trap and a patient interface assembly connector in connected and disconnected states, according to a representative embodiment.

FIG. 2 provides top, side and end plan views of a removable water trap, according to a representative embodiment. FIG. 3 is an exploded perspective view of a removable water trap, according to a representative embodiment. FIG. 4 provides perspective views of a removable water trap and a tether assembly receptacle, in disconnected and connected states, according to a representative embodiment. FIG. 5 provides perspective views of a removable water trap and a patient interface assembly connector, in connected and disconnected states, according to a representative embodiment.

Referring to FIGS. 2 to 5, the water trap 110 includes the housing 111, which provides a first portion 210 and a second portion 220 on opposite ends. As mentioned above, the first portion 210 is configured to be removably inserted into the tether assembly receptacle 132 of the tether assembly 130, enabling delivery of the (filtered) respiratory gas stream to the gas analysis bench 120. In the depicted embodiment, the first portion 210 defines at least one groove, indicated by representative groove 215, on an outer surface of the housing 111. The groove 215 is configured to slidably communicate with a guide bump 415 protruding from an inner diameter of a receptacle opening 411 in the tether assembly receptacle 132, as shown in FIG. 4. Although one groove 215 is shown in FIGS. 2 to 4, it is understood that the first portion 210 of the housing 111 may define two or more grooves, without departing from the scope of the present teachings. For example, the first portion 210 may have a second groove on a circumferentially opposite side of the housing 111, which slidably communicates with a guide bump 416 protruding from the inner diameter of the receptacle opening 411, as shown FIG. 4. Also, although the guide bump 416 is shown directly opposite the guide bump 415 on the inner diameter of the receptacle opening 411, it is understood that the guide bumps 415 and 416 (as well as corresponding grooves) may be arranged at various locations with respect to one another, and/or additional guide bumps (and corresponding grooves) may be included, without departing from the scope of the present teachings.

In the depicted embodiment, the groove 215 is curved, requiring a turning motion of the housing 111 to enable the entire length of the groove 215 to slide along the guide bump 415 while pushing the first portion 210 of the housing 111 into the tether assembly receptacle 132. The curve of the groove 215 is "J" shaped, where a substantially straight portion 217 initially guides the first portion 210 of the housing 111 into the receptacle opening 411 by communicating with the guide bump 415, and a curved end portion 218 defines the turning motion of the housing 111, enabling a locking feature. The groove 215 may also include an entry portion 219, which provides an expanded opening for initially guiding the groove 215 onto the guide bump 415. For example, the entry portion 219 may include converging sides that guide the guide bump 415 into the straight portion 217. The push-to-turn geometry on water trap 110 enables large variability of the insertion position. The water trap 110, when installed from substantially any orientation, will find its own center, and lock within a quarter of a turn, for example. The water trap 110 may bottom out on bezel attachment or housing 440 preventing over-tightening.

In alternative embodiments, the groove 215 may be straight (having no curves) or may define a curved shape different than that depicted in FIGS. 2 to 4, without departing from the scope of the present teachings. For example, the groove 215 may be "L" shaped, where the locking feature includes making a substantially right degree angle from an initial straight portion. In various embodiments, the locking feature may provide a tactile response when the first portion 210 of the housing 111 is fully engaged with the tether assembly receptacle 132, such as a snapping or seating sensation. For example, the first portion 210 is fully engaged when the guide bump 415 is positioned at the end of the curved end portion 218. The downstream water trap connector 116 extends from the end of the housing 111, and may be attached to an insertable filter tube 365, as discussed below with reference to FIG. 3.

The upstream water trap connector 115 is arranged at the opposite end of the housing 111. In the depicted embodiment, the upstream water trap connector 115 includes the second portion 220 of the housing 111, tabs 254, 255, protruding member 256 and seal member 257, for example. The second portion 220 of the housing 111 includes at least one flange, indicated by representative flanges 221 and 222, extending beyond an outer perimeter of the first portion 210 of the housing 111. The flanges 221 and 222 are arranged on substantially opposite sides of the second portion 220 in order to accommodate a turning motion of the housing 111, for example, when a turning motion is needed to slidably communicate the groove 215 with the guide bump 415, as discussed above. The flanges 221 and 222 may align with corresponding visual alignment indicators 421 and 422 on the tether assembly receptacle 132 when the first portion 210 of the housing 111 is fully engaged or locked with the tether assembly receptacle 132, as shown in FIG. 4.

The second portion 220 also defines a cutout portion 224 adjacent the at least one flange 221, 222. In the depicted embodiment, the cutout portion 224 is a substantially "C" shaped cutout between the flanges 221 and 222. The protruding member 256 of the upstream water trap connector 115 extends from the cutout portion 224, and the seal member 257 circumferentially surrounds the protruding member 256. The seal member 257 may be formed as a rigid feature and part of the protruding member 256. The downstream patient interface connector 143 of the extension line 148 would then be made of a soft elastomeric material. When the protruding member 256 and the seal member 256 are fit into the flexible downstream patient interface connector 143, a pneumatic seal is made. The downstream patient interface connector 143 may have a corresponding groove (not shown) on an inner surface of the pneumatic opening. In another embodiment, the seal member 257 may be formed of an elastomeric material, which compresses when fit into the downstream patient interface connector 143 of the extension line 148, providing the pneumatic seal. In this embodiment, the downstream patient interface connector 143 may be made of a more rigid material. For example, the seal member 257 may communicate with a corresponding groove (not shown) in an inner surface of an opening in the downstream patient interface connector 143. In addition, the depicted embodiment includes connector tabs, indicated by the representative connector tabs 254 and 255, protruding from an inner surface of the cutout portion 224. The connector tabs 254 and 255 are configured to fit into corresponding slots (not shown) of the downstream patient interface connector 143. The connector tabs 254 and 255 may provide a tactile response when the upstream water trap connector 115 is fully engaged with the downstream patient interface connector 143. The connection between the upstream water trap connector 115 and the downstream patient interface connector 143 is discussed further with reference to FIG. 5, below.

Referring to FIG. 3, the water trap 110 further includes a filter assembly 360. The filter assembly 360 is configured to remove moisture (filter) from the respiratory gas stream. In the depicted embodiment, the filter assembly 360 includes a filter tube 365 insertably contained within the housing 111. The filter tube 365 may be injection molded, formed of a relatively soft or compliant material, such as thermoplastic elastomer, rubber, or flexible PVC, for example. Hydrophilic material 366 is arranged in the filter tube 365 for absorbing moisture from the respiratory gas stream. Hydrophobic material 367 is also arranged in the filter tube 360, adjacent the hydrophilic material 366, for blocking moisture in the respiratory gas stream not absorbed by the hydrophilic material 366. For example, the hydrophilic material 366 may repel moisture (or treated with a chemical to repel moisture) and/or may swell when wet in order to block the moisture in the respiratory gas stream. In the depicted embodiment, each of the hydrophilic material 366 and hydrophobic material 367 are substantially tubular in shape, so that they fit into the filter tube 365. Other arrangements of the hydrophilic material 366 and the hydrophobic material 367 may be included, such as the hydrophobic material 367 concentrically surrounding the hydrophilic material 366, without departing from the scope of the present teachings. In various embodiments, the hydrophilic material 366 may include polyester/polyester fiber and the hydrophobic material 367 may include sintered polyethylene, for example, available from Porex Corporation. Notably, by forming the filter tube 365 of compliant material, the filter elements, such as the hydrophilic mater 366 and the hydrophobic material 367, are encapsulated in the compliant material within rigid material of the filter assembly 360. Thus, manufacturing tolerances of the filter elements may be more easily accommodated and pressure drop of the filter elements is not adversely impacted by compressing the filter elements.

In an embodiment, the entire water trap 110 may be replaceable as a whole. Because the filter assembly 360 is not part of the patient interface module 140, as in conventional systems, it may be replaced independently of the patient interface module 140, including the patent accessories, which are changed on a patient-by-patient basis, thus saving time and materials. In other words, the filter assembly 360 may be maintained according to its own use schedule, as opposed to being a disposable part of the patient interface module 140. In other embodiments, part of the filter assembly 360 could be readily removable and replaceable, so that new hydrophilic material 366 and/or hydrophobic material 367 may be provided in the water trap 110 after one or more uses by one or more patients. Different portions of the filter assembly 360 may be replaced according to various embodiments. For example, the entire filter assembly 360 may be replaceable, or the entire filter tube 365 may be replaceable, or only the hydrophilic material 366 and/or hydrophobic material 367 within the filter tube 365 may be replaceable, without departing from the scope of the present teachings.

In the depicted embodiment, one end of the filter tube 365 includes the downstream water trap connector 116 that provides a connection to the tether line 136 of the tether assembly 130 via an opening within the tether assembly receptacle 132. The downstream water trap connector 116 may be a seal tip, for example, configured to provide a gas tight or pneumatic seal between the water trap 110 and the tether assembly receptacle 132. The filter assembly 360 thus enables connection of the water trap 110 to the tether assembly module 130 for delivering the respiratory gas, with the moisture removed, to the sample cell 134 via the tether line 136. The downstream water trap connector 116 may include a shoulder portion 235 and a tip portion 237. The tip portion 237 may have stacked concentric layers configured to communicate with a corresponding opening in the tether assembly receptacle 132 up to the shoulder portion 235. The concentric layers may be formed of elastomeric material, for example, which compresses in the tether assembly receptacle 132 to provide a pneumatic seal when the water trap 110 is fully engaged with the tether assembly receptacle 132. Of course, other configurations of the downstream water trap connector 116 may be provided without departing from the scope of the present teachings.

Referring to FIG. 4, the tether assembly receptacle 132 includes a housing 440 and at least one flange, indicated by representative flanges 441 and 442, extending from an outer surface of a main portion of the housing 440. The flanges 441 and 442 are arranged on substantially opposite sides of the housing 440 in order to accommodate the turning motion when inserting the water trap 110, as discussed above. The flanges 441 and 442 may coincide with the visual alignment indicators 421 and 422, respectively, so that they align with the flanges 221 and 222 of the second portion 220 of the housing 111 when the first portion 210 of the housing 111 is fully engaged (and locked) with the tether assembly receptacle 132, e.g., as shown in the bottom depiction of FIG. 4. The tether assembly receptacle 132 may further include a hex nut 450 for fastening the housing 440 in place, e.g., on a front panel of a respirator. The tether line 136 is connected to the back side of the housing 440, and is accessible via a hole (not shown) through the housing 440 to form a pneumatic seal with the downstream water trap connector 116 of the water trap 110, as discussed above.

Referring to FIG. 5, the water trap 110 is shown inserted in the tether assembly receptacle 132. In addition, the upstream water trap connector 115 of the water trap 110 and the downstream patient interface connector 143 of the extension line 148 are shown in connected and disconnected states. In the depicted embodiment, the downstream patient interface connector 143 includes housing 540 having a rounded portion 541 configured to fit complementarily with the cutout portion 224 defined by the second portion 220 of the housing 111 of the water trap 110. The housing 540 may be made from a soft, conforming elastomeric material, for example. The rounded portion 541 and the cutout portion 224 are both substantially "C" shaped, so that the rounded portion 541 fits between the flanges 221 and 222, although other shapes may be incorporated without departing from the scope of the present teachings.

The housing 540 of the downstream patient interface connector 143 further includes shoulder portions 521 and 522 against which the flanges 221 and 222 are seated when the downstream patient interface connector 143 is connected to the upstream water trap connector 115. In addition, the downstream patient interface connector 143 includes an opening (not shown) configured to receive the protruding member 256 (and the seal member 257) extending from the cutout portion 224 of the water trap 110, enabling the upstream water trap connector 115 to provide a pneumatic seal for communication with the extension line 148 via an opening in the downstream patient interface connector 143. Also, the shoulder portions 521 and 522 may define slots (not shown) for receiving connector tabs 254 and 255 protruding from the inner surface of the cutout portion 224, as discussed above. There are no secondary components required to create the pneumatic seal between the upstream water trap connector 115 and the downstream patient interface connector 143, reducing overall cost and reliability of the connection.

Figure 6:
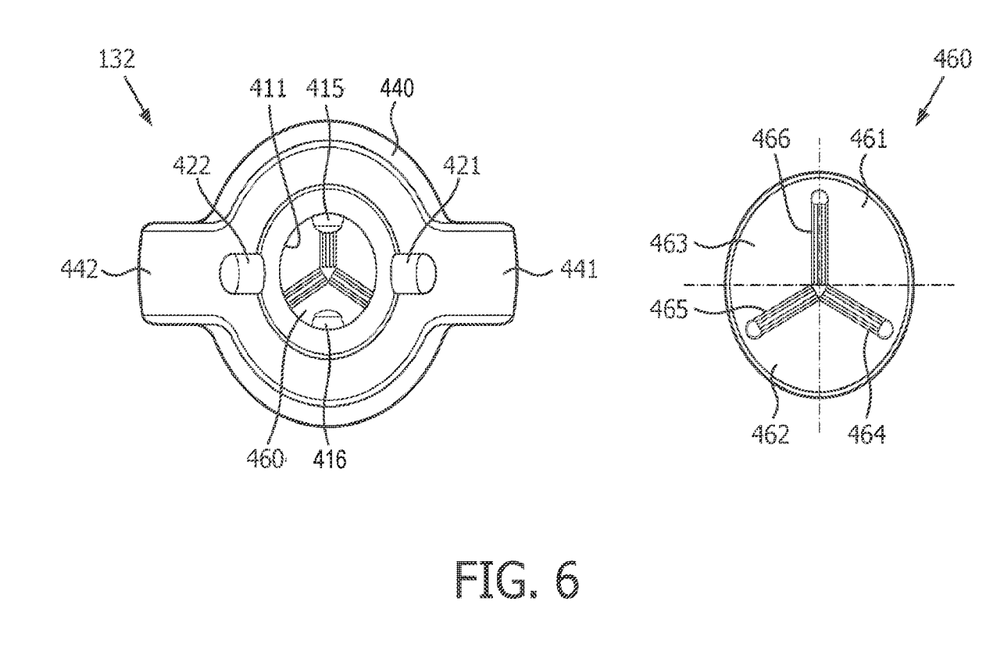
FIG. 6 provides end plan views of a tether assembly receptacle, according to a representative embodiment.

When the water trap 110 is not inserted in the receptacle opening 441, the tether assembly receptacle 132 is susceptible to contamination from the outside environment without a cover over the receptacle opening 441. FIG. 6 provides end plan views of the tether assembly receptacle and a cover, according to a representative embodiment.

Referring to FIG. 6, an end perspective view of the tether assembly receptacle 132 shows the housing 440, the flanges 441 and 442 extending from the outer perimeter the housing 440, and the visual alignment indicators 421 and 422. The housing 440 defines the receptacle opening 411, and guide bumps 415 and 416 protrude from opposite sides of the inner surface of the receptacle opening 411, as discussed above.

In addition, the tether assembly receptacle 132 includes cover 460, shown in the closed position (without the water trap 110 inserted). The cover 460 includes flexible lobes separated by corresponding slits, indicted by representative lobes 461 to 463 and slits 464 to 466. The lobes 461 to 463 may be formed of a resilient elastomeric material, so that they are self-closing. Thus, the lobes 461 to 463 deform from a closed position upon insertion of the first portion 210 of the housing 111 into the receptacle opening 411, separating from one another along the slits 464 to 466, and return to the closed position upon removal of the first portion 210 of the housing 111. The lobes 461 to 463 in the closed position protect the tether assembly receptacle 132, for example, preventing contaminants from entering the receptacle opening 411, when the water trap 110 is not inserted. Although FIG. 5 depicts three lobes 464 to 466, it is understood that any number of lobes may be included without departing from the scope of the present teachings.

Figure 7:
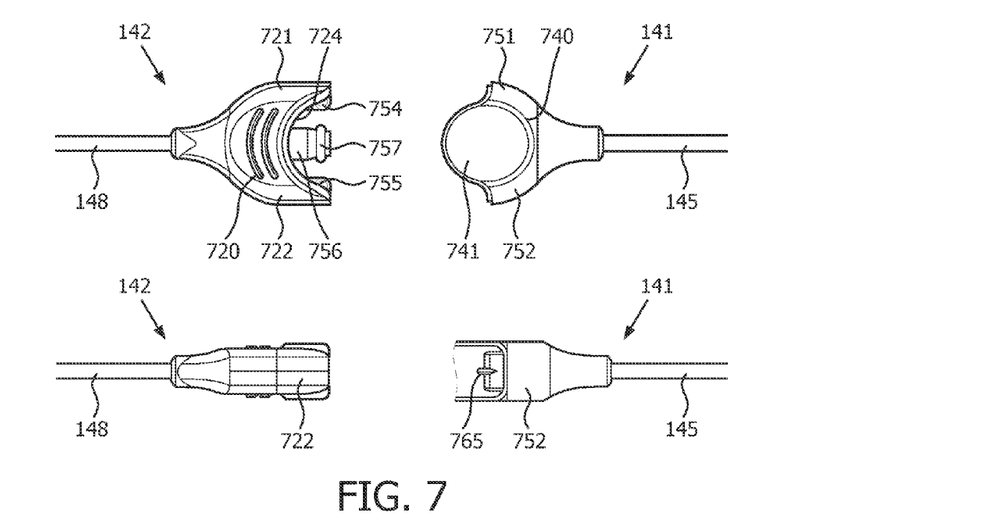
FIG. 7 provides top and side plan views of in-line patient interface line and patient accessories connectors in a disconnected state, according to a representative embodiment.
Figure 8:
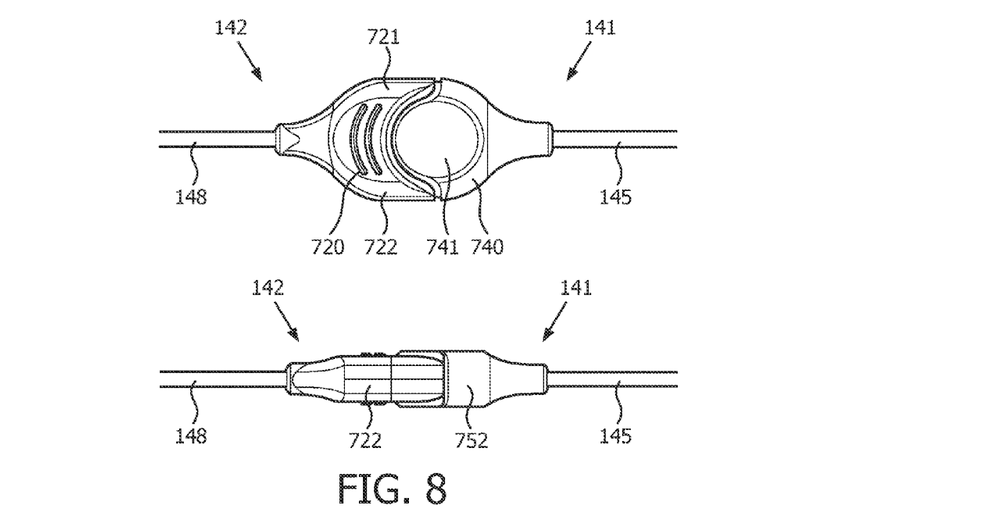
FIG. 8 provides top and side plan views of in-line patient interface line and patient accessories connectors in a connected state, according to a representative embodiment.
Figure 9:
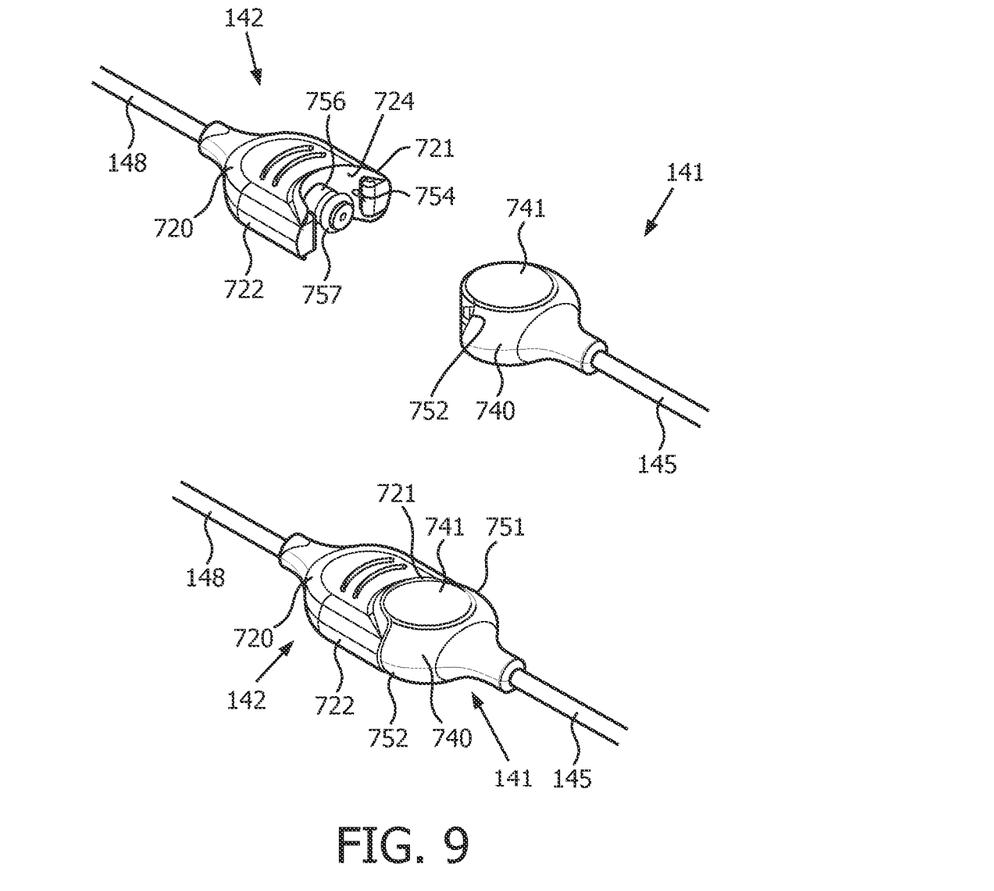
FIG. 9 provides perspective views of in-line patient interface line and patient accessories connectors in disconnected and connected states, according to a representative embodiment.

The various lines that attach to one another, such as the upstream patient interface connector 142 and the downstream patient interface connector 141, likewise require pneumatic connections. FIG. 7 provides top and side plan views of a patient interface line connector and a patient accessories connector in a disconnected state, according to a representative embodiment. FIG. 8 provides top and side plan views of a patient interface line connector and a patient accessories connector in a connected state, according to a representative embodiment. FIG. 9 provides perspective views of a patient interface line connector and a patient accessories connector in disconnected and connected states, according to a representative embodiment.

Referring to FIGS. 7 to 9, the upstream patient interface connector 142 of the extension line 148 is variously shown in connected and disconnected states with the downstream patient interface connector 141 of the airway 145. Notably, in the depicted embodiment, the configuration of the upstream patient interface connector 142 is substantially the same as that of the upstream water trap connector 115 and the configuration of the downstream patient interface connector 141 is substantially the same as that of the downstream patient interface connector 143, discussed above, although other connector configurations may be incorporated without departing from the scope of the present teachings.

In the depicted embodiment, the upstream patient interface connector 142 includes housing 720, tabs 754, 755, protruding member 756 and seal member 757, for example. The housing 720 includes at least one flange, indicated by representative flanges 721 and 722, arranged on substantially opposite sides of the housing 720. The housing 720 also defines a cutout portion 724 adjacent the at least one flange 721, 722. In the depicted embodiment, the cutout portion 724 is a substantially "C" shaped cutout between the flanges 721 and 722. The protruding member 756 of the upstream patient interface connector 142 extends from the cutout portion 724, and the seal member 757 circumferentially surrounds the protruding member 756. The seal member 757 may be made from a rigid material as part of the protruding member 756 with the downstream patient interface connector 141 formed of an elastomeric material. In another embodiment, the seal member 757 may be formed of an elastomeric material, which compresses when fit into the downstream patient interface connector 141, providing a pneumatic seal. The seal member 757 may communicate with a corresponding groove (not shown) in an inner surface of an opening in the downstream patient interface connector 141. In addition, the depicted embodiment includes connector tabs, indicated by the representative connector tabs 754 and 755, protruding from an inner surface of the cutout portion 724. The connector tabs 754 and 755 are configured to fit into corresponding slots, such as slot 765, of the downstream patient interface connector 141. The connector tabs 754 and 755 may provide a tactile response when the upstream patient interface connector 142 is fully engaged with the downstream patient interface connector 141.

The downstream patient interface connector 141 includes housing 740 having a rounded portion 741 configured to fit complementarily with the cutout portion 724 defined by the housing 720. The housing 740 may be made from a soft, conforming elastomeric material, for example. The rounded portion 741 and the cutout portion 724 are both substantially "C" shaped, so that the rounded portion 741 fits between the flanges 721 and 722, although other shapes may be incorporated without departing from the scope of the present teachings. The housing 740 of the downstream patient interface connector 141 further includes shoulder portions 751 and 752 against which the flanges 721 and 722 are seated when the downstream patient interface connector 141 is connected to the upstream patient interface connector 142.

In addition, the downstream patient interface connector 141 includes an opening (not shown) configured to receive the protruding member 756 (and the seal member 757) extending from the cutout portion 724 of the housing 720, enabling the upstream patient interface connector 142 to provide a pneumatic seal for communication with the airway 145 via an opening in the downstream patient interface connector 141. Also, the shoulder portions 751 and 752 may define slots, indicated by slot 765, for respectively receiving the connector tabs 754 and 755 protruding from the inner surface of the cutout portion 724, as discussed above. There are no secondary components required to create the pneumatic seal between the upstream patient interface connector 142 and the downstream patient interface connector 141, reducing overall cost and reliability of the connection.

According to various embodiments, the water filter or water trap of a sidestream respiratory gas analyzer is removed from the patient interface assembly into a replaceable (disposable) cartridge. Also, the sampling chamber may be moved from the patient accessory to the gas analysis bench via a replaceable tether assembly. No voids or extra internal area that is out of the sample flow path remain, creating a low-deadspace design. This low deadspace filter cartridge and sampling chamber are replaced only as needed, as opposed to every time the patient interface is replaced, lowering the overall cost of the patient interfaces.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

What is claimed:

1. A removable water trap device for removing moisture from a respiratory gas stream received from a patient interface assembly, enabling monitoring of at least one gas within the respiratory gas stream by an analysis bench, the device comprising:
   a housing comprising a first portion being insertably attachable to a tether assembly receptacle to enable connection of the device to the analysis bench for delivering the respiratory gas stream via a tether line;
   an upstream water trap connector attachable to a downstream patient interface connector of a sample flow line in the patient interface assembly for receiving the respiratory gas stream via the sample flow line; and
   a filter assembly insertably contained within the housing and configured to remove moisture from the respiratory gas stream, the filter assembly comprising a downstream water trap connector attachable with the tether line within the tether assembly receptacle, wherein the filter assembly is replaceable independently of replacement of the patient interface assembly.

2. The device of claim 1, wherein the first portion of the housing is insertable into a receptacle opening defined by the tether assembly receptacle.

3. The device of claim 2, wherein the first portion of the housing defines at least one groove on an outer surface of the housing, configured to slidably communicate with a guide bump protruding from an inner surface of the receptacle opening.

4. The device of claim 3, wherein the at least one groove is curved, requiring a turning motion of the housing to enable the at least one groove to slidably communicate with the guide bump.

5. The device of claim 4, wherein the at least one groove comprises a locking feature configured to provide a tactile response when the first portion of the housing is fully engaged with the tether assembly receptacle.

6. The device of claim 4, wherein the upstream water trap connector comprises a second portion of the housing defining at least one flange extending beyond the outer surface of the first portion of the housing, the at least one flange accommodating the turning motion of the housing.

7. The device of claim 6, wherein the second portion further defines a cutout portion adjacent the at least one flange, and wherein the upstream water trap connector further comprises a protruding member extending from the cutout portion of the second portion of the housing, and insertable into an opening in the downstream patient interface connector.

8. The device of claim 7, wherein the upstream water trap connector her comprises a seal member circumferentially surrounding the protruding member and configured to provide a pneumatic seal with the sample flow line in the downstream patient interface connector.

9. The device of claim 8, wherein the seal member is configured to communicate with a corresponding groove in an inner surface of the opening in the downstream patient interface connector.

10. The device of claim 7, wherein the upstream water trap connector further comprises at least one tab extending from an inner surface of the cutout portion, the at least one tab being configured to communicate with a corresponding slot in the downstream patient interface connector, the at least one tab providing a tactile response when the upstream water trap connector is fully engaged with the downstream patient interface connector.

11. The device of claim 6, wherein the at least one flange aligns with a corresponding visual alignment indicator on the tether assembly receptacle when the first portion of the housing is fully engaged with the tether assembly receptacle.

12. The device of claim 1, wherein the filter assembly comprises: a filter tube insertably contained within the housing, one end of the filter tube comprising the downstream water trap connector configured to provide a pneumatic seal with the tether line in the tether assembly receptacle; a hydrophilic material arranged in the filter tube for absorbing moisture from the respiratory gas stream; and a hydrophobic material arranged in the filter tube for blocking moisture in the respirator gas stream not absorbed by the hydrophilic material.

13. A sidestream respiratory gas analysis system comprising:
   a removable water trap for removing moisture from a respiratory gas stream received from a patient interface assembly;
   a gas analysis bench for detecting and analyzing at least one gas in the respiratory gas stream; and
   a tether assembly connected between the gas analysis bench and the patient interface assembly for providing the respiratory gas stream to the gas analysis bench, the tether assembly comprising a tether assembly receptacle configured to receive the water trap,
   wherein the water trap comprises:
      a housing comprising a first portion insertable into a receptacle opening in the tether assembly receptacle, enabling delivery of the respiratory gas stream to the gas analysis bench via the tether assembly;
      a filter assembly insertable into the housing and configured to remove moisture from the respiratory gas stream, the filter assembly comprising a filter tube insertably contained within the housing, at least one material contained in the filter tube configured to remove and/or block moisture from the respiratory gas stream, and a downstream water trap connector on one end of the filter tube for connecting the filter assembly to the tether assembly via the tether assembly receptacle for delivering the respiratory gas, with the moisture removed; and an upstream water trap connector for connecting the water trap to the patient interface assembly for receiving the respiratory gas stream.

14. The sidestream respiratory gas analysis system of claim 13, wherein the housing defines at least one groove on an outer surface, the at least one groove being configured to slidably communicate with a corresponding guide bump protruding from an inner surface of the receptacle opening for locking the first portion of the housing in the tether assembly receptacle.

15. The sidestream respiratory gas analysis system of claim 14, wherein the housing further comprises a second portion comprising at least one flange extending beyond the outer surface of the first portion of the housing and defining a cutout portion adjacent the at least one flange, the cutout portion being configured to fit complementarily with a rounded portion of a downstream patient interface assembly connector, and wherein the upstream water trap connector comprises a protruding member extending from the cutout portion and insertable into an opening of a downstream connector of the patient interface assembly.

16. The sidestream respiratory gas analysis system of claim 15, wherein the upstream water trap connector further comprises at least one tab extending from an inner surface of the cutout portion of the second portion, the at least one tab being configured to communicate with a corresponding slot in the downstream connector of the patient interface assembly to provide a tactile response when the protruding member is fully engaged with a corresponding opening in the downstream connector of the patient interface assembly.

17. The sidestream respiratory gas analysis system of claim 13, wherein the tether assembly further comprises a plurality of flexible lobes covering the receptacle opening, the first portion of the housing being insertable into the receptacle opening through the plurality of lobes, and
wherein the plurality of flexible lobes are self-closing, so that the plurality of flexible lobes close to cover the receptacle opening when the first portion of the housing is not inserted.

18. The sidestream respiratory gas analysis system of claim 14, wherein the patient interface assembly comprises an extension line, the extension line including a dryer, and a patient interface comprising an airway, or one of a nasal cannula, a nasal-oral sampling cannula or a nasal-oral with oxygen delivery nasal cannula, wherein a downstream patient interface connector is attached to a downstream end of the extension line.

19. The sidestream respiratory gas analysis system of claim 18, wherein the patient interface assembly further comprises an upstream patient interface connector attached to an upstream end of the extension line and configured to connect with a downstream patient interface connector on the airway, and wherein the upstream patient interface connector comprises a housing defining at least one flange and a cutout portion adjacent the at least one flange, the cutout portion being configured to fit complementarily with a rounded portion of the downstream patient interface connector of the airway, and a protruding member extending from the cutout portion and insertable into an opening of the downstream patient interface connector.

20. A removable water trap device for removing moisture from a respiratory gas stream received from a patient interface assembly, enabling monitoring of at least one gas within the respiratory gas stream by an analysis bench, the device comprising:

a housing comprising first and second portions, the first portion being insertable into an opening in a tether assembly receptacle, enabling connection of the water trap device to the analysis bench for delivering the respiratory gas stream via a tether line, the housing defining a plurality of grooves configured to slidably communicate with a corresponding plurality of guide bumps protruding from an inner surface of the opening in the tether assembly receptacle, wherein each of the plurality of grooves is curved, requiring application of a turning motion of the housing to lock the first portion of the housing into the tether assembly receptacle;

a filter assembly insertably contained within the housing and configured to remove moisture from the respiratory gas stream, the filter assembly comprising an insertable filter tube contained within the housing, at least one material contained in the filter tube configured to remove moisture from the respiratory gas stream, and a seal tip on one end of the filter tube configured to connect to the tether line within the tether assembly receptacle; and a connector comprising the second portion of the housing, and attachable to a complementary connector of the patient interface assembly for receiving the respiratory gas stream via a sample flow line, wherein the insertable filter tube passes through at least a part of each of the first and second portions of the housing.

* * * * *